United States Patent [19]
Taylor

[11] Patent Number: 6,156,424
[45] Date of Patent: Dec. 5, 2000

[54] COHESIVE PRODUCTS

[75] Inventor: Paul Taylor, North Andover, Mass.

[73] Assignee: Andover Coated Products, Inc., Salisbury, Mass.

[21] Appl. No.: 08/961,801

[22] Filed: Oct. 31, 1997

[51] Int. Cl.⁷ ............................................. B32B 7/12
[52] U.S. Cl. .......................... 428/355 R; 427/207.1; 427/208.4; 528/480; 442/59
[58] Field of Search ............... 442/59, 149; 428/343, 428/355 R; 427/207.1, 208.4; 528/480

[56] References Cited

U.S. PATENT DOCUMENTS

| | | | |
|---|---|---|---|
| 2,485,725 | 10/1949 | Francis, Jr. | 154/48 |
| 2,687,723 | 8/1954 | Stem | 128/169 |
| 2,811,154 | 10/1957 | Scholl | 128/156 |
| 3,033,201 | 5/1962 | Olsen | 128/156 |
| 3,356,635 | 12/1967 | Heer | 260/32.8 |
| 3,464,543 | 9/1969 | Kwiatanowski, Jr. | 206/59 |
| 3,468,748 | 9/1969 | Bassett | 161/122 |
| 3,575,782 | 4/1971 | Hansen | 161/141 |
| 3,649,436 | 3/1972 | Buese | 161/160 |
| 3,697,315 | 10/1972 | Mine | 117/122 P |
| 3,763,858 | 10/1973 | Buese | 128/156 |
| 3,912,676 | 10/1975 | Brizzolara et al. | 260/27 BB |
| 3,925,283 | 12/1975 | Dahl | 260/24 |
| 4,414,970 | 11/1983 | Berry | 128/156 |
| 4,497,926 | 2/1985 | Toy | 524/271 |
| 4,552,802 | 11/1985 | Mechin | 428/255 |
| 4,556,595 | 12/1985 | Ochi | 428/143 |
| 4,623,416 | 11/1986 | Henning et al. | 156/331.7 |
| 4,653,492 | 3/1987 | Parsons | 128/155 |
| 4,679,519 | 7/1987 | Linville | 114/103 |
| 4,803,240 | 2/1989 | Midgley et al. | 524/504 |
| 4,810,745 | 3/1989 | Pike et al. | 524/516 |
| 4,851,459 | 7/1989 | Ramalingam | 523/414 |
| 4,859,521 | 8/1989 | Pike et al. | 428/195 |
| 4,889,884 | 12/1989 | Dust et al. | 524/314 |
| 4,902,370 | 2/1990 | Dust et al. | 156/327 |
| 5,006,401 | 4/1991 | Frank | 428/231 |
| 5,153,049 | 10/1992 | Groshens | 428/196 |
| 5,156,589 | 10/1992 | Langen et al. | 602/77 |
| 5,209,801 | 5/1993 | Smith | 156/161 |
| 5,227,409 | 7/1993 | Mobley et al. | 521/167 |
| 5,265,445 | 11/1993 | Shytles et al. | 66/192 |
| 5,297,296 | 3/1994 | Moretz et al. | 2/237 |
| 5,352,216 | 10/1994 | Shiono et al. | 604/312 |
| 5,476,896 | 12/1995 | Pereira et al. | 524/524 |
| 5,616,400 | 4/1997 | Zhang | 428/195 |
| 5,670,260 | 9/1997 | Zajaczkowski et al. | 428/345 |
| 5,692,937 | 12/1997 | Zhang | 442/149 |
| 5,762,623 | 6/1998 | Murphy et al. | 602/75 |

FOREIGN PATENT DOCUMENTS

| | | |
|---|---|---|
| 14079 | 1/1990 | Japan . |
| 653921 | 5/1951 | United Kingdom . |
| 1033115 | 6/1966 | United Kingdom . |
| 1034439 | 6/1966 | United Kingdom . |
| 2256785 | 12/1992 | United Kingdom . |
| WO 97/04154 | 2/1997 | WIPO . |
| WO 97/23249 | 7/1997 | WIPO . |

OTHER PUBLICATIONS

Database WPI, Week 9009, Derwent Publications Ltds., London, GB; AN 90–062345 and JP 2014079 to Du Pont KK (See Abstract).

Gritter, M., "Latex Allergy," *Lippincotts Primary Care Practice* 1(2):142–151 (1997).

Posch, A. et al., Characterization and Identification of Latex Allergens by Two–Dimensional Electrophoresis and Protein Microsequencing, *J. Allergy Clin, Immunol.,* 99(3)385–395 (1997).

Stevenson, A., "Crystallization in Elastomers at Low Temperatures", *Handbook of Polymer Science and Technology,* 2:61–98 (1989), Chermisinoff, Nicholas P., ed.

*Primary Examiner*—Elizabeth M. Cole
*Attorney, Agent, or Firm*—Hale and Dorr LLP

[57] ABSTRACT

A cohesive product that has one or more layers of a substrate and a synthetic water-based cohesive polymer that is applied to the substrate and defines an outer surface of the product. The synthetic water-based cohesive polymer is an inherently crystalline elastomer whose polycrystalline structure has been disrupted such that the elastomer possesses a cohesive property.

6 Claims, 2 Drawing Sheets

COHESIVE PRODUCTS

This invention is directed to cohesive products, and more particularly to cohesive tapes and bandages, in which the cohesive material is a synthetic elastomer rather than natural rubber latex.

BACKGROUND OF THE INVENTION

Natural rubber latex is widely used in the healthcare industry, from surgical gloves to bandages. Because of the unique combination of strength, flexibility, and elasticity of natural rubber, it is typically the material of choice for a variety of medical products. In particular, all known available cohesive bandages are composed at least partly of natural rubber latex. Natural rubber latex is inherently cohesive, meaning that it sticks to itself rather than to other materials. The available adhesive bandages that are entirely free of natural rubber use pressure-sensitive adhesives and are not cohesive.

A small but significant segment of the population develops immediate or delayed allergic reactions to natural rubber. Recently, the United States Food and Drug Administration ruled that all medical devices containing natural rubber latex must be labeled with warnings that the latex can cause allergic reactions. This regulation was issued amid more than 1,700 reports of severe allergic reactions to latex in medical devices that the FDA has received over the past decade. Proteins of natural rubber latex cause IgE-mediated sensitization in 3% to 18% of health care workers and in up to 50% of patients with spina bifida. See Glitter, M., Latex Allergy, Lippincotts Primary Care Practice 1(2):142–151 (1997), which is hereby incorporated by reference. It is believed that plant proteins remaining in products made of natural rubber latex are potential sensitizers. See Posch, A. et al., Characterization and identification of latex allergens by two-dimensional electrophoresis and protein microsequencing, J. Allergy Clin. Immunol. 99(3):385–395 (1997), which is also hereby incorporated by reference. A further disadvantage of using natural rubber latex instead of synthetic latex alternatives is that natural rubber latex degrades, particularly when exposed to petroleum derivative products such as petrolatum, and animal fats. Synthetic latexes, such as polychloroprene, exhibit an enhanced chemical resistance, which natural rubber based products do not possess.

There thus is a real and long-standing need for a cohesive bandage or other product that is free of and thus avoids the allergy-causing proteins found in natural rubber latex and the petroleum-caused degradations of natural rubber latex, yet still possesses the desirable cohesive properties of natural rubber. There is a particular need for such bandages which employ a synthetic elastomeric cohesive that, like natural rubber latex, is water-based and can be employed using procedures similar to those now widely used in connection with the manufacture of natural rubber latex cohesive bandages.

SUMMARY OF THE INVENTION

Applicant has found that there is a correlation between the level of cohesion and the physical and chemical structure of an elastomeric polymer, and that the desired cohesive properties found in natural rubber are largely due to the fact that natural rubber latex has a polycrystalline structure.

Although most synthetic elastomers and latexes cannot be compounded to produce the same types of cohesion as natural rubber, i.e., compounding most synthetic latexes produces a pressure sensitive adhesive, applicant has further discovered that similar cohesive properties may be obtained by compounding synthetic water-based elastomers that have polycrystalline structures similar to those of natural rubber.

Accordingly, it is a primary object of the present invention to produce a cohesive tape, bandage or other product that is free from natural rubber by utilizing the crystallization properties of synthetic elastomers to produce synthetic water-based cohesive polymers.

In one aspect, the invention provides a cohesive product comprising one or more layers of a substrate and a cohesive material in which the cohesive material is a synthetic water-based elastomer rather than natural rubber latex. The synthetic water-based cohesive polymer defines at least one outer surface of the product, and is usually applied to the substrate in such a way as to provide a cohesive surface on both the opposite sides of the product.

In one embodiment of this aspect, this invention provides a product in which the synthetic water-based cohesive is an inherently crystalline elastomer to which at least one tackifying agent has been added in an amount effective to disrupt the crystalline structure of the elastomer and to maintain the elastomer in a partial crystalline state such that the elastomer possesses a cohesive property.

In preferred embodiments of this aspect, a tape/bandage or other substrate is coated or impregnated through the thickness of the substrate with a dispersion/emulsion of the elastomeric matrix before the water is evaporated (e.g., before drying), the cohesiveness of the synthetic elastomer is controlled by the addition of two tackifying agents with different melting points, or molecular weights, and the tape substrate material(s) is one or more of a woven or knitted fabric, a warp-knitted weft-insertion fabric, a non-woven material, paper, and a surface-treated polymeric.

Yet another aspect of the invention provides a method of modifying the cohesiveness of a synthetic water-based elastomer that is inherently capable of crystallization by:

(1) combining the synthetic water-based elastomer with at least one tackifying agent to produce a dispersion/emulsion of the elastomer and tackifying agent(s), the tackifying agent(s) being present in the dispersion/emulsion in an amount effective to disrupt the crystalline structure of the elastomer and to maintain the elastomer in a partial polycrystalline state; and (2) evaporating the water from the dispersion/emulsion (typically by heat-treating the dispersion/emulsion) to produce a cohesive elastomeric solid.

Other objects, features and advantages of this invention will be apparent to those of ordinary skill in the art in view of the following Detailed Description, taken together with the attached drawings.

DETAILED DESCRIPTION OF THE INVENTION

Figure 1:
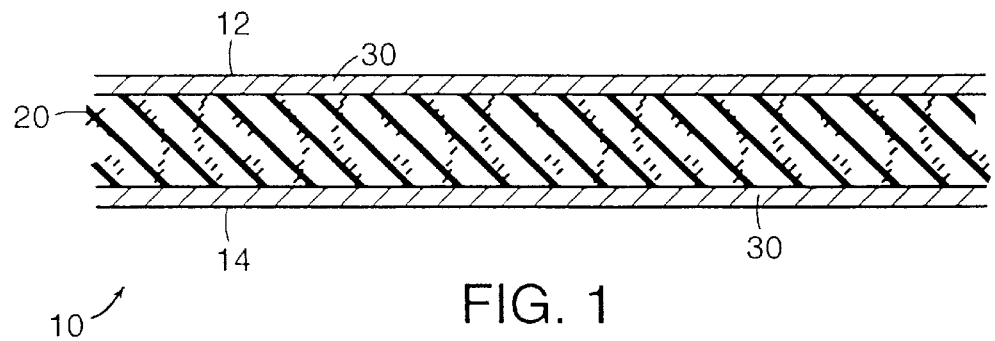
FIG. 1 is a cross-sectional view of a first embodiment of the invention, in which a multi-layered substrate has been impregnated with a synthetic cohesive, water-based elastomer.
Figure 2:
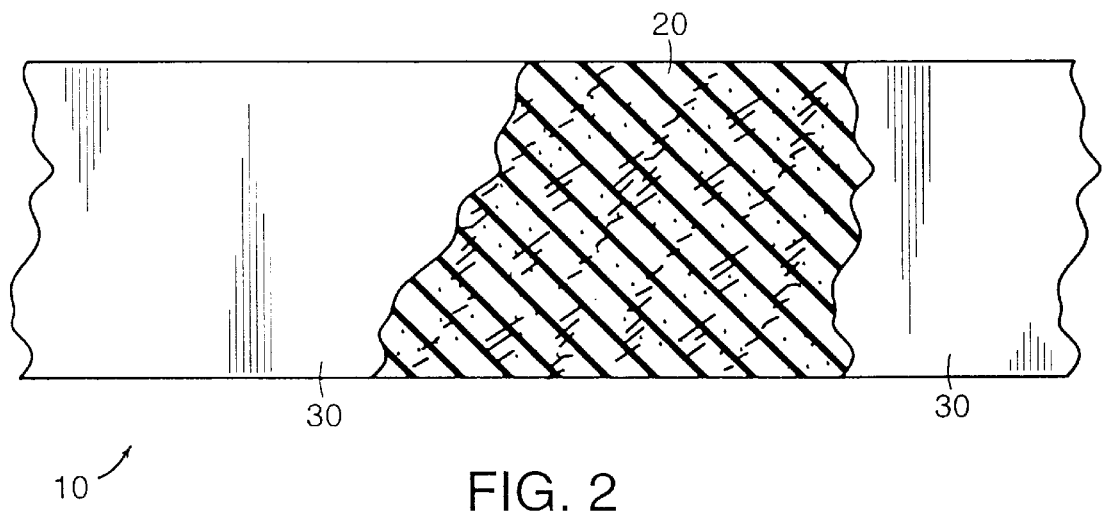
FIG. 2 is a top view of the embodiment of FIG. 1.

Referring more particularly to the drawings, FIG. 1 is a cross-sectional view of a tape/bandage, generally designated 10, in which a substrate 20 has been impregnated through the thickness of the substrate with a synthetic, cohesive, water-based elastomer 30. The substrate 20 is of the type sold by Andover Coated Products Inc. of Salisbury, Mass. under the trademark "POWERFLEX" and described in copending U.S. patent application Ser. No. 08/504,098, filed Jul. 19, 1995, which is hereby incorporated by reference. As described in this prior patent application, the substrate includes a plurality of longitudinally-extending elastic threads or yarns sandwiched between a layer of a warp-knit (weft-insertion) fabric and a layer of a non-woven fabric. In the present embodiment, the cohesive elastomer 30 bonds the three layers together. The elastomer 30 also extends fully through the thickness of the substrate, so that the top and bottom surfaces of the overall tape-bandage 10 are defined by the synthetic elastomer 30. FIG. 2 is a top view of the tape bandage 20 of FIG. 1, cut away so as to better show each of the three layers of the substrate 20.

Figure 3:
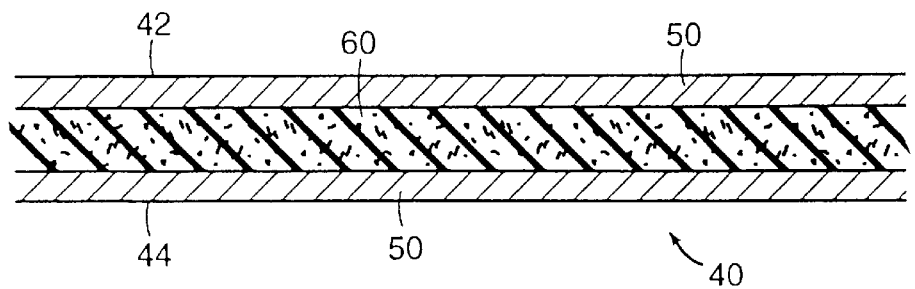
FIG. 3 is a cross-sectional view of a second embodiment comprising a knitted substrate and a synthetic cohesive, water-based elastomer that is deposited on the opposite sides of a single layer of knitted substrate, such as by spraying or coating.

FIG. 3 is a cross-sectional view of a second tape/bandage, generally designated 40, in which a synthetic, cohesive, water-based elastomer 50 has been coated or sprayed onto the opposite sides of a single layer of a woven or knitted substrate 60. As with the embodiment of FIG. 1, it will be recognized that the top and bottom surfaces 42, 44 of the overall tape/bandage 40, are defined by the synthetic elastomer. Since the substrate is only a single layer, however, the elastomer is not required to bond a multi-layer structure together and need not extend through the thickness of the substrate.

Because the synthetic elastomers 30, 50 of FIGS. 1 and 3, respectively, are cohesive, it will be recognized that the outer surfaces of the tapes 10, 40 of FIGS. 1 and 3, respectively, will stick to each other, e.g., the top surface 12 of tape 10 will stick to bottom surface 14 when the tape is wrapped around, for example, a user's ankle; and the top surface 42 of tape 40 will similarly stick to bottom surface 44. However, because the synthetic elastomers are cohesive, rather than pressure sensitive, the surfaces of tapes 10, 40 will not stick (at least to any significant degree) to other surfaces or materials.

It will be recognized that substrates 20, 60 may be made of any of a wide range of materials, and may have a wide range of structures. For example, any of the one or more layers of a substrate may be, for example, a woven, knitted, warp-knit (weft-insertion) or non-woven fabric, or paper. It may also be a surface-treated polymeric, such as a sheet of linear, low-density polyethylene ("LLDPE") or linear, low-density polypropylene ("LLDPP"), one or more surface of which has been treated to insure adhesion to the elastomeric cohesive. Similarly, the substrate structure may be elasticized, either as described above with reference to FIG. 1, by knitting or weaving elastic threads into one or more of the layers, or by knitting or sewing elastomeric threads through a single or multi-layer substrate.

In embodiments in which the cohesive product of the present invention is a tape or bandage, the substrate typically will comprise a woven, knitted, or warp-knit (weft insertion) fabric, or a non-woven fabric such as a non-woven scrim, of either natural or synthetic fiber. In one embodiment in this aspect, the substrate comprises a single layer of a non-woven fabric wherein threads are knitted through the fabric and a synthetic cohesive, water-based elastomer is deposited on opposite sides of the fabric by, for instance, spraying or coating. In a preferred tape/bandage, the substrates 20, 60 comprise nylon or polyester.

In another embodiment of this aspect, the substrate of the tape/bandage comprises a first and a second layer of non-woven fabric and a third layer which is elastic in a direction extending longitudinally of the tape/bandage, said third layer being in between the first and second layers of non-woven fabric.

In a further embodiment, the substrate of the tape/bandage comprises: a first layer of warp-knitted (weft insertion) fabric oriented with the knit yarns extending longitudinally of the tape/bandage; a second layer of a non-woven fabric; and a third layer which is elastic in a direction extending longitudinally of the tape/bandage, the third layer being between said first and second layers.

As discussed above, it is well known to make tapes/bandages similar to those shown in FIGS. 1 and 3 in which the cohesive material is natural rubber latex. In general, such tapes/bandages are made from a water-based emulsion of a natural rubber latex to which a tackifier has been added. The resulting latex/tackifier structure is applied to the substrate (typically by saturating the substrate with the emulsion or coating the emulsion onto the opposite sides of the substrate), and the structure is then dried to produce the desired end product.

The tapes/bandages and other products of the present invention are preferably made using the same general manufacturing techniques, except that, as discussed below in more detail, the elastomer is a synthetic water-based elastomer rather than natural rubber latex, and different tackifiers and/or tackifier quantities are employed to enhance the cohesive property of the elastomer by disruption of the crystalline structure and to maintain the cohesive material in the desired partial polycrystalline state. More specifically, in the practice of the present invention, the synthetic cohesive end product is typically made by:

(1) combining a synthetic, inherently crystalline elastomer with at least one tackifying agent to produce a dispersion/emulsion of the elastomer and tackifying agent(s);
(2) providing a substrate of a desired structure;
(3) treating the substrate with the dispersion/emulsion such that the dispersion/emulsion defines at least one outer surface of the product; and
(4) evaporating water from the dispersion/emulsion so that the dispersion/emulsion to produce a cohesive elastomeric solid.

As previously mentioned, it is well known that natural rubber latex can be cohesive. It has also been recognized that polyisoprene (natural rubber) is inherently capable of crystallization. See Cheremisinoff, Nicholas P., ed., Handbook of Polymer Science and Technology 2:61–98 (1989) which is hereby incorporated by reference.

The crystalline structure of certain polymeric elastomers is not a structure as organized as a single crystal of, for example, sodium chloride, but rather is a plurality of ordered structures in a mass of amorphous polymer. As applied to polymers, the terms crystalline, microcrystalline, and polycrystalline refer to ordered structures which develop within a mass of otherwise amorphous polymeric material. Certain polymers such as isotactic polypropylene develop a highly organized microcrystalline structure due to the inherent structure of the polypropylene. The term microcrystalline, as used herein, refers to ordered structures that can be observed under magnification of thin films of polymer. The term polycrystalline, as used herein, means that many microcrystallites are present in a mass of polymer. As used herein, "inherently crystalline" or "inherently capable of crystallization" means that a material exhibits a microcrystalline, polycrystalline, or crystalline-like structure in a stable, natural form.

Figure 4:
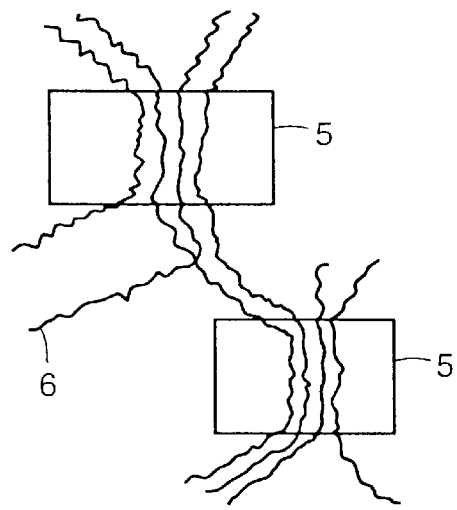
FIG. 4 depicts the crystalline structure of an elastomer inherently capable of crystallization. Long chains of the elastomer come together to develop ordered structures in an otherwise amorphous mass of elastomer.

In the case of elastomers such as natural rubber latex, poly-cis 1, 4, 2-methyl butadiene (poly cis-1, 4 isoprene), crystalline structures develop in the otherwise amorphous mass of natural rubber. These structures can be envisioned to develop where molecules in the mass align themselves in a definite order as shown in FIG. 4. Regions of order 5 among chains of elastomer 6 are held together by secondary valence forces producing a strengthening of the overall structure.

Figure 5:
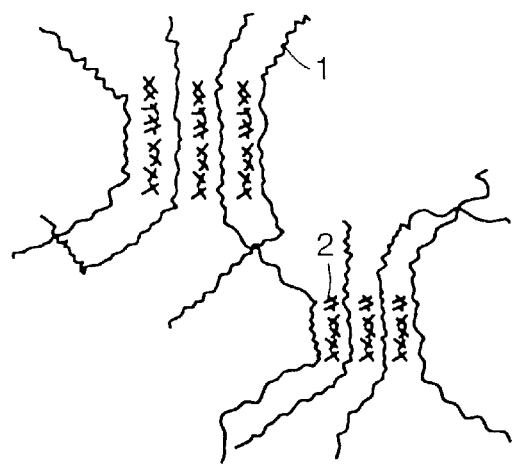
FIG. 5 depicts the partial crystalline structure of an elastomer to which one or more tackifying agent has been added. Shorter chains of the tackifiers are shown interspersed with longer chains of the elastomer, disrupting the crystalline-like structures present in the elastomer by spreading the elastomeric chains farther apart. Although not as structured as the elastomer depicted in FIG. 4, the matrix of elastomer and tackifier displays a level of structured, partial polycrystallinity.

It has been known that these structures can be disrupted to a greater or lesser extent by use of heat, or a combination of heat and the addition of lower molecular weight and/or lower melting point materials, often referred to as "tackifiers" or "tackifying agents." These include for example, esters of abietic acid (rosin esters), certain low-molecular weight hydrocarbon resins usually referred to as $C_5$–$C_9$ polymers, polymers with low glass transition temperatures such as some acrylic polymers and some butadiene-styrene copolymers, and certain monomeric plasticizers. The structure of the natural rubber may be disrupted by blending one or more of the lower molecular weight and/or lower melting point materials listed above with the rubber polymer, and then drying at room temperature or common drying temperature, i.e. at or above the boiling point of the water carrier. This disruption of the polycrystalline structures is illustrated by FIG. 5, wherein the polymeric elastomer (natural rubber) chains I are represented by long lines and the tackifying resins 2 are represented by short lines.

Figure 6:
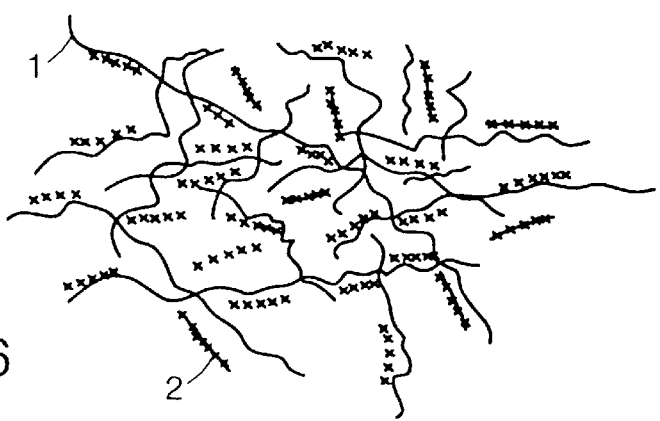
FIG. 6 depicts an elastomer whose crystalline structure has been completely disrupted by the presence of a relatively large amount of tackifier(s) resulting in an unordered, amorphous mass with pressure-sensitive properties.

As the result of extensive experimentation, applicant found that cohesiveness and crystallinity are related, i.e., that the cohesive property of natural rubber latex (and also of other inherently crystalline synthetic polymers as discussed below) depends on the natural rubber latex being in a stable crystalline-like state. Although the exact reason for this relationship between crystallinity and cohesiveness has not previously been determined, it appears that the interaction of tackifiers and plasticizers with the natural rubber latex (and, as discussed below, also with inherently crystalline, synthetic elastomers such as polychloroprene) partially disrupts the polycrystalline-like structures, making them first cohesive and with increasing amount of tackifiers, pressure-sensitive. This disruption of the crystalline structure of the natural rubber latex by the tackifying agents causes the aligned structures to spread out, maintaining the latex in a partially polycrystalline state but without destroying the aligned structures entirely. If the amount of tackifier added to the rubber is such that the crystalline structures in the natural rubber are completely disrupted, the mass becomes amorphous and pressure sensitive, as shown in FIG. 6. Long chains of the elastomer 1 and relatively shorter chains of tackifiers 2 are shown to exist as an amorphous mass lacking an ordered structure. If, on the other hand, there is a high level of ordered crystalline structuring in the natural rubber, the rubber becomes non-cohesive. These two extremes define a "window," within which the rubber has cohesive properties.

Applicant evaluated many synthetic polymeric materials which are not inherently crystalline, such as noncrystallizing polyurethanes, polyacrylates, butadiene styrene, acrylonitrile copolymer, carboxylated butadiene styrene, vinyl acetate acrylate copolymer, styrene acrylic copolymers, and acrylic polyurethanes, and found that none resulted in a cohesive water-based product. Applicant then focused on finding polymers which possess crystalline properties similar to natural rubber. This led to the identification of two classes of crystallizing polymers, namely water-based polychloroprene emulsions such as poly-2-chloro, 1–4 butadiene and certain water based polyurethanes, that are inherently capable of crystallization, i.e., polyester polyurethane and polycaprolactone polyurethane. Applying the knowledge gained in producing cohesive elastomeric materials from natural rubber, applicant determined that one could indeed disrupt the crystallinity of these inherently crystalline elastomeric polymers and thus bring them to, and arrest them in, a structure that had a desired level of partial polycrystallinity (e.g., through the use of tackifying resins); and that, like natural rubber latex, these synthetic inherently crystalline materials exhibit a cohesive property when the degree of partial polycrystallinity is maintained in a range (typically determined empirically) between a completely amorphous state and a highly crystalline state.

The tackifiers used to produce cohesive forms of these synthetic elastomeric materials are of the same type used in connection with natural rubber, although the amount(s) of any particular tackifier(s) used to form a stable cohesive will vary within empirically defined limits. Applicant found that the window of cohesiveness for polychloroprene is narrower than that of natural rubber latex. As the examples discussed below demonstrate, exceeding the limits produces either a non-cohesive or an amorphous pressure-sensitive adhesive, neither of which is useful for the present invention. Applicant also determined that partially crystalline polychloroprene was more stable in a cohesive state than were inherently crystalline polyurethanes.

In preferred practices of the invention, the inherently crystalline, water-based, synthetic elastomer is preferably polychloroprene, such as DuPont NEOPRENE LTX-654, and the tackifying resins used to arrest it in the desired polycrystalline state are one or more of a rosin ester derivative, a petroleum derivative, a hydrocarbon resin, an acrylic polymer, a butadiene-based polymer or a combination of one or more types such as rosin ester/hydrocarbon resin.

As used in the present invention, the terms "tackifier" and "tackifying agent" herein refer to a class of thermoplastic polymers used to affect the characteristics of a finished polymeric product and includes the tackifying resins listed above, naturally occurring rosins, rosin esters, and plasticizers. As used in the present invention, the term "rosin" as used herein refers to a naturally occurring material extracted from stumps of pine trees whose principal component is abietic acid. The term "rosin ester" as used herein, refers to the carboxyl group of abietic acid which has been esterified with aromatic and aliphatic alcohols. The term "hydrocarbon resins" as used herein refers to lower-molecular-weight thermoplastic polymers derived from cracked petroleum distillates, terpene fractions, coal tar, and a variety of pure monomers. Although a single tackifying resin can be used, blends of two or more with different melting points (and molecular weights) have been found to produce cohesive products with better final properties. In some circumstances, plasticizers may be used in lieu of one or more tackifier resins. Synthetic elastomers such as NEOPRENE LTX-654 and tackifying agents are commercially available in dispersion and emulsion forms.

When compounding the elastomer and tackifiers, there exists for each elastomer a "window" of compounding in which the structure of the polychloroprene or other elastomer is crystalline, and within which the degree of crystallinity can be modified so that the material has cohesive properties. The extent of the "window" varies depending on the particular elastomer, and is determined empirically. At one extreme of the "window," the elastomer becomes non-cohesive, and at the other extreme, it becomes pressure-sensitive. The state of the material within its "window" depends on the extent to which the polycrystalline structure of the polychloroprene or other elastomer is disrupted, and can be varied using different amounts and types of tackifying agents. For any particularly water-based inherently crystalline, synthetic elastomer, the amount and type of tackifier required to arrest the elastomer in a partially crystalline, cohesive state is empirically determined, using tackifiers and protocols similar to those long employed in the production of cohesive natural rubber latex materials and known to one of skill in the art.

When applied to a substrate so that it defines the outer surfaces of a product, a water-based, synthetic inherently crystalline elastomer to which an effective amount of tackifier has been added produces a cohesive product which will adhere to itself, but not (at least to any significant degree) to other substrates.

The following Examples will further illustrate the invention. The Examples are not intended, and should not be interpreted, to limit the scope of the invention which is more fully defined in the claims which follow.

EXAMPLE I

Preparation of Synthetic Water-Based Elastomeric Products

Elastomers, specifically polychloroprene elastomers produced by DuPont under the names NEOPRENE LTX-654 and NEOPRENE LTX-400 sold in dispersion or emulsion form, were diluted with water to obtain approximately 50% total solids per liquid weight elastomer mixture. At least one tackifying agent or agents were added to each elastomer mixture and the mixture was sufficiently agitated at room temperature for approximately 15 minutes to produce a homogeneous emulsion of elastomer, water, and tackifying agent(s). The tackifying agent(s) used were rosin ester resins or a combination of rosin ester and hydrocarbon resin, sold in dispersion or emulsion form as the following: Hercules TACOLYN 1070 (a rosin ester resin), Hercules TACOLYN 5001 (a rosin ester resin), Eka Nobel SNOTAK 780G (a rosin ester resin), Eka Nobel 342-B (a rosin ester resin), and Neville Alliance PERMATAK H712 (a combination of rosin ester resin and hydrocarbon resin). The TACOLYN 5001 and SNOTAK 780G resins have higher molecular weights and melting points (i.e., melting point not less than about 80° C.) than the 342-B and PERMATAK H712 resins (i.e. melting point no more than about 70° C.). A thickening agent, e.g. ammonium polyacrylate solution or sodium polyacrylate solution, was added to the homogeneous emulsion and agitated to produce an elastomeric material that has a viscosity of approximately 1000–1500 centipoise (cps).

It was found that the cohesive properties of polychloroprene were improved when two tackifying resins with melting points higher and lower relative to one another were added to the polychloroprene. The best results using polychloroprene DuPont NEOPRENE LTX-654 were obtained with a higher melting point resin (approximately 85° C.), Eka Nobel SNOTAK 780 (rosin ester resin), in an amount between 8 and 25% total liquid weight, preferably 18.6%, and a lower melting point resin (approximately 70° C.), Neville Alliance PERMATAK H712 (a combination rosin ester resin/hydrocarbon resin derivative), in an amount between 4 and 10% total liquid weight, preferably 7.9%.

The cohesive properties of the polychloroprenes were tested on a fabric, preferably a cotton cloth sheet laid on a flat surface, on which a bead of elastomeric material prepared as above was placed. A blade applicator, e.g. UNIVERSAL blade applicator was calibrated to approximately 8–12 mm. The blade of the blade applicator was drawn across the surface of the fabric, smoothing and spreading the elastomeric material uniformly across the surface of the fabric at a thickness of approximately 8–12 mm. The fabric containing the elastomeric material was then dried at 117° C. for approximately 2–5 minutes to produce the finished elastomeric product.

Determining Cohesive Bond Strength

The cohesive bond strength of a finished elastomeric product was determined by two methods: T-Peel test and shear bond test.

1) T-Peel Test:

Two strips of the finished elastomeric product measuring 1 inch in width and of equal length, were placed face to face and a cylindrical weight was rolled across the surface of the superimposed strips. The two non-superimposed ends were clamped in the jaws of a tensile testing apparatus and pulled linearly in opposite directions pulling the two strips apart. The resistance of the superimposed strips to the movement of the clamps was measured in ounces/inch of width.

2) Shear Bond Test:

Two strips of the finished elastomeric product measuring 1 inch in width and of equal length, were placed linearly so the end of one strip overlapped the end of another strip by 1 inch lengthwise. A cylindrical weight was rolled across the surface of the superimposed end of the two strips. The non-superimposed end of the two strips were clamped in the jaws of a tensile testing apparatus and pulled linearly in opposite directions. The strength of the shear bond of the superimposed ends was measured in lbs/sq. in.

The results of the T-Peel and the shear bond tests for DuPont NEOPRENE LTX-654 with Eka Nobel SNOTAK 780G as the higher melting point tackifying resin and Neville Alliance PERMATAK H712 as the lower melting point resin, are given in Table 1 as follows:

TABLE 1

| | |
|---|---|
| T-Peel: | >25 ounces/linear inch of finished elastomeric material |
| Shear bond: | >25 pounds/square inch of finished elastomeric material |

Table 2 shows the cohesive property of finished synthetic elastomeric materials using DuPont NEOPRENE LTX-654, for three different formulation ratios of Eka Nobel SNOTAK 780G, a rosin ester tackifying resin, as the higher melting point tackifying resin, and Neville Alliance PERMATAK H712, a combination rosin ester/hydrocarbon resin derivative, as the lower melting point tackifying resin. The amount of elastomer and tackifier is measured as a percentage of total liquid weight of the elastomer and tackifiers combined.

TABLE 2

|  | Non-Cohesive | Lightly Cohesive | Very Cohesive | Cohesive, Edge of Pressure Sensitivity |
|---|---|---|---|---|
|  | (Liquid Weight Parts per Hundred) | | | |
| Polychloroprene Latex: DuPont NEOPRENE LTX-654 | 100 | 88 | 73.5 | 65 |
| Higher melting point tackifier: SNOTAK 780G |  | 8 | 18.6 | 25 |
| Lower melting point tackifier: PERMATAK H712 |  | 4 | 7.9 | 10 |

As summarized by Table 2, polychloroprene latex itself, i.e., without any tackifier or plasticizer, is non-cohesive; a cohesive material can be produced by adding one or more tackifiers, and the cohesive properties depend on the amount and type of tackifier used. To produce a cohesive elastomer using DuPont NEOPRENE LTX-654, the amount of the higher melting point tackifier, Eka Nobel SNOTAK 780G, is preferably between 8 and 25 percent of total liquid weight and the amount of the lower melting point tackifier, Neville Alliance PERMATAK H712, is preferably between 4 and 10 percent of total liquid weight.

EXAMPLE II

The cohesiveness of synthetic elastomers was modified by the addition of one or more tackifiers. The stable form of the elastomer is less crystalline than it would be without the addition of tackifiers. The addition of the tackifiers arrests the elastomer in a partial crystalline state that is less crystalline than its most favored crystalline form by virtue of the tackifiers spreading the crystallites present in the elastomeric matrix farther apart.

Two examples of polychloroprene were chosen for study. These were NEOPRENE LTX-400 and NEOPRENE LTX-654 from DuPont-Dow Elastomers. LTX-400 is a fast crystallizing polymer and LTX-654 is a medium crystallizing polymer. The higher total solids contained in LTX-654 and the ease of tackifying it to achieve cohesive properties made LTX-654 the material of choice.

Various formulations of tackifiers and tackifier blends were analyzed with DuPont NEOPRENE LTX-654 and DuPont NEOPRENE LTX-400 as the synthetic elastomer. The results of the series of experiments utilizing different kinds of tackifying resins with NEOPRENE LTX-654 and NEOPRENE LTX-400 and the cohesive property associated with each formulation is given below in Tables 3 and 4 for LTX-654 and LTX-400, respectively. Applicant determined that the window of cohesive properties available with the polychloroprene is narrower than with natural rubber latex. As shown in Tables 3 and 4, below, when properly compounded, the polychloroprene latexes LTX-654 and LTX-400 can be shown to exhibit one of the following cohesive qualities, depending on the amount of tackifier used:

(1) Non-cohesive, that is, it does not stick to itself;

(2) Lightly cohesive, wherein it barely sticks to itself;

(3) Very cohesive, where it has aggressive self-adhesion without adhering to other substrates; and (4) Cohesive but bordering on the edge of pressure-sensitivity, wherein the material has aggressive self-adhesion and also adheres slightly to other substrates.

(5) Pressure-sensitive, wherein the material aggressively adheres to other substrates.

Good cohesion was achieved for formulations comprising LTX-654 and the tackifying resins, Eka Nobel SNOTAK 780G and Neville Alliance PERMATAK H712, as measured by touch-testing. T-Peel and shear bond test results are also given where available.

TABLE 3

| Trial 1: | |
|---|---|
| NEOPRENE LTX-654: | 92.6% |
| Tackifier SNOTAK 780G: | 7.4% |
| Cohesiveness: | Non-cohesive |
| Trial 2: | |
| NEOPRENE LTX-654: | 74.0% |
| Higher m.p. tackifier SNOTAK 780G: | 17.0% |
| Lower m.p. tackifier PERMATAK H712: | 9.0% |
| Cohesiveness: | Cohesive, on the edge of pressure-sensitivity |
| Trial 3: | |
| NEOPRENE LTX-654: | 73.5% |
| Higher m.p. tackifier SNOTAK 780G: | 18.6% |
| Lower m.p. tackifier PERMATAK H712: | 7.9% |
| Cohesiveness: | Very cohesive |
| Trial 4: | |
| NEOPRENE LTX-654: | 76.0% |
| Higher m.p. tackifier TACOLYN 1070: | 16.0% |
| Lower m.p.. tackifier PERMATAK H712: | 8.0% |
| Cohesiveness: | Cohesive, on the edge of pressure-sensitivity |
| Trial 5: | |
| NEOPRENE LTX-654: | 79.4% |
| Higher m.p. tackifier TACOLYN 1070: | 13.7% |
| Lower m.p. tackifier PERMATAK H712: | 6.9% |
| T-Peel: | 18 oz/linear inch |
| Shear Bond: | 40 lbs/sq. inch |
| Cohesiveness: | Very cohesive |
| Trial 6: | |
| NEOPRENE LTX-654: | 74.0% |
| Tackifier TACOLYN 5001: | 26.0% |
| T-Peel: | 56 oz/linear inch |
| Shear Bond: | 61 lbs/sq. inch |
| Cohesiveness: | Very cohesive |
| Trial 7: | |
| NEOPRENE LTX-654: | 74.0% |
| Tackifier Eka Nobel 342-B: | 26.0% |
| Cohesiveness: | Pressure-Sensitive |

It is well-known that tackifying agents increase the level of adhesive strength of a polymer, or "tack," hence the name, and that increasing the amount of tackifying agent generally increases the adhesiveness. It is not well-known, however, how combinations of more than one tackifying agent may affect the overall property of a particular polymer or elastomer. Extensive research by applicant with natural rubber latex and polychloroprene has shown that good cohesion occurs when the tackifying agent(s) comprise roughly 20–30% total liquid weight. Using this range estimate of tackifying agent as a guide, applicant has identified the borderline between cohesion and pressure-sensitivity for various formulations of LTX-654 and LTX-400 and tackifying resins. Applicant was also able to determine that the cross-over from cohesion to pressure-sensitivity occurs rapidly, and that stable, cohesive properties were maintained successfully when tackifying resins comprised about 20–25% of total liquid weight.

As shown by Trials 4 and 5, adding 13.7% total liquid weight of Hercules TACOLYN 1070 and 6.9% total liquid weight of Neville Alliance PERMATAK H712 (totalling 20.6% per total liquid weight of tackifiers) to LTX-654 resulted in an elastomeric product having good cohesion, whereas a formulation using 24% total tackifier resins resulted in a cohesive product bordering on the edge of pressure-sensitivity. Similarly, as shown by Trials 6 and 7, adding 26.0% per total liquid weight of the resins Hercules TACOLYN 5001 and Eka Nobel 342-B to LTX-654 produced cohesive and pressure-sensitive elastomers, respectively. Applicant was able to determine from these trials that the cross-over point between cohesiveness and pressure-sensitivity was in this weight range.

Applicant also determined, however, that simply increasing the total amount of tackifier does not necessarily result in an increase in cohesive strength. As shown by Trial 2 of Table 3, adding 18.6% of Eka Nobel SNOTAK 780G and 7.9% Neville Alliance PERMATAK H712 (total amount of tackifying resins comprising 26.5% total liquid weight) resulted in a product exhibiting good, stable cohesion. As shown by Trial 3 of Table 3, when the amount of the higher melting point tackifying resin was reduced to 16% and the amount of lower melting point tackifier resin increased to 8.0% (total amount of tackifying resins comprising 24.0%), however, the resulting product was cohesive but at the edge of pressure-sensitivity. Thus, although a smaller amount of total tackifying resins was used, an increase in adhesive strength was observed.

This result can be explained by the fact that tackifying agents with lower melting points ("lower m.p.") generally have a lower average molecular weight than tackifying agents with higher melting points ("higher m.p."). Thus, although the total amount of tackifying resins used in Trial 2 of Table 3 was greater than that used in Trial 3 of Table 3, there was also a lesser amount of lower melting point resin in Trial 2 for increasing the overall cohesive strength. On a molar basis, lower molecular weight resins are typically more effective in increasing the adhesive strength of a polymer than higher molecular weight ones.

Applicant's finding of the cross-over threshold between cohesiveness and pressure-sensitivity allowed applicant to produce for the first time, a synthetic water-based elastomeric cohesive. Applicant also determined that a formulation with substantially less than 20% total liquid weight of tackifying resins will produce a non-cohesive product. As shown in Trial 1 of Table 3, a formulation comprising only LTX-654 or LTX-400, or less than roughly 20% total liquid weight of tackifying resin resulted in a non-cohesive product.

TABLE 4

| | |
|---|---|
| NEOPRENE LTX-400: | 80.0% |
| Tackifier TACOLYN 5001: | 20.0% |
| Cohesiveness: | Non-cohesive |
| NEOPRENE LTX-400: | 77.3% |
| Tackifier TACOLYN 5001: | 22.7% |
| Cohesiveness: | Cohesive; became lightly cohesive after 24 hours |
| NEOPRENE LTX-400: | 72.5% |

TABLE 4-continued

| | |
|---|---|
| Higher m.p. tackifier TACOLYN 5001: | 23.5% |
| Lower m.p. tackifier PERMATAK H712: | 4.0% |
| Cohesiveness: | Cohesive; became lightly cohesive after 24 hours |

Experiments with LTX-400, a high chlorine content polychloroprene that readily and rapidly crystallizes in its stable form, demonstrated that cohesion is readily obtainable but that sustained cohesion is more difficult to achieve. This is due to the strong tendency of LTX-400, by virtue of its many chlorine bonds, to revert to a highly crystalline state. It is believed that a stable, cohesive product may readily be obtained by increasing the amount of total tackifying resins used. Experiments directed to such are currently underway.

The various technical and scientific terms used herein have meanings that are commonly understood by one of ordinary skill in the art to which the present invention pertains. As is apparent from the foregoing, a wide range of suitable materials and/or methods known to those of skill in the art can be utilized in carrying out the present invention; however, preferred materials and/or methods have been described. Materials, substrates, and the like to which reference is made in the foregoing description and examples are obtainable from commercial sources, unless otherwise noted. Further, although the foregoing invention has been described in detail by way of illustration and example for purposes of clarity and understanding, these illustrations are merely illustrative and not limiting of the scope of the invention. Other embodiments, changes and modifications, including those obvious to persons skilled in the art, will be within the scope of the following claims.

What is claimed is:

1. A cohesive product comprising a substrate and a synthetic water-based cohesive, said water-based cohesive comprising (a) an elastomer having an inherently crystalline structure and defining at least one outer surface of the product and selected from the group consisting of polychloroprene, polyester polyurethane, and polycaprolactone polyurethane, and (b) two tackifying resins with melting points higher and lower relative to one another in an amount effective to disrupt the crystalline structure of the elastomer, maintaining the elastomer in a partial polycrystalline state such that the elastomer possesses a cohesive property.

2. A cohesive product comprising a substrate and a synthetic water-based cohesive, said water-based cohesive comprising (a) an elastomer having an inherently crystalline structure and defining at least one outer surface of the product and selected from the group consisting of polychloroprene, polyester polyurethane, and polycaprolactone polyurethane, and (b) two tackifying agents with average molecular weights higher and lower relative to one another in an amount effective to disrupt the crystalline structure of the elastomer and to maintain the elastomer in a partial polycrystalline state such that the elastomer possesses a cohesive property.

3. A cohesive product comprising a substrate and a synthetic water-based cohesive defining at least one outer surface of the product, wherein the synthetic water-based cohesive comprises an elastomer having an inherently crystalline structure and consists essentially of polychloroprene, polyester polyurethane, or polycaprolactone polyurethane, and at least one tackifying agent in an amount effective to disrupt the crystalline structure of the elastomer and maintain the elastomer in a partial polycrystalline state such that the elastomer possesses a cohesive property.

4. A cohesive product comprising a substrate and a synthetic water-based cohesive defining at least one outer surface of the product, wherein the synthetic water-based cohesive comprises an elastomer having an inherently crystalline structure and is selected from the group consisting of polychloroprene, polyester polyurethane, and polycaprolactone polyurethane, and at least one tackifying agent in an amount effective to disrupt the crystalline structure of the elastomer and maintain the elastomer in a partial polycrystalline state such that the elastomer possesses a cohesive property.

5. A method of modifying cohesiveness of a synthetic water-based elastomer inherently capable of crystallization, wherein the elastomer consists essentially of polychloroprene, polyester polyurethane, or polycaprolactone polyurethane by:

(1) combining the synthetic water-based elastomer with at least one tackifying agent to produce a dispersion/emulsion of the elastomer and tackifying agent(s), the tackifying agents being present in the dispersion/emulsion in an amount effective to disrupt the crystalline structure of the elastomer an maintain the elastomer in a partial polycrystalline state; and (2) evaporating the water from the dispersion/emulsion to produce a cohesive elastomeric solid.

6. A method of making a synthetic cohesive product comprising the steps of:

(1) combining a synthetic, inherently crystalline elastomer, wherein the elastomer consists essentially of polychloroprene, polyester polyurethane, or polycaprolactone polyurethane with at least one tackifying agent to produce an emulsion/dispersion of the elastomer and tackifying agent(s);

(2) providing a substrate of a desired structure;

(3) treating the substrate with the dispersion/emulsion such that the dispersion/emulsion defines at least one outer surface of the product; and (4) evaporating water from the dispersion/emulsion to produce a cohesive elastomeric solid.

* * * * *

(12) INTER PARTES REVIEW CERTIFICATE (116th)
United States Patent
Taylor

(10) Number: US 6,156,424 K1
(45) Certificate Issued: Jan. 13, 2016

(54) COHESIVE PRODUCTS

(75) Inventor: Paul Taylor

(73) Assignee: ANDOVER HEALTHCARE, INC.

Trial Number:
  IPR2014-00630 filed Apr. 15, 2014

Petitioner: 3M COMPANY, INC.

Patent Owner: ANDOVER HEALTHCARE, INC.

Inter Partes Review Certificate for:
  Patent No.: 6,156,424
  Issued: Dec. 5, 2000
  Appl. No.: 08/961,801
  PCT Filed: Oct. 31, 1997

The results of IPR2014-00630 are reflected in this inter partes review certificate under 35 U.S.C. 318(b).

INTER PARTES REVIEW CERTIFICATE
U.S. Patent 6,156,424 K1
Trial No. IPR2014-00630
Certificate Issued Jan. 13, 2016

AS A RESULT OF THE INTER PARTES REVIEW PROCEEDING, IT HAS BEEN DETERMINED THAT:

Claim 6 is cancelled.

\* \* \* \* \*